United States Patent
Engell

(10) Patent No.: US 8,415,510 B2
(45) Date of Patent: Apr. 9, 2013

(54) SYNTHESIS OF A PEG-6 MOIETY FROM COMMERCIAL LOW-COST CHEMICALS

(75) Inventor: Torgrim Engell, Oslo (NO)

(73) Assignee: GE Healthcare Limited, Buckinghamshire (GB)

(*) Notice: Subject to any disclaimer, the term of this patent is extended or adjusted under 35 U.S.C. 154(b) by 0 days.

(21) Appl. No.: 12/918,391

(22) PCT Filed: Feb. 10, 2009

(86) PCT No.: PCT/US2009/033620
§ 371 (c)(1),
(2), (4) Date: Aug. 19, 2010

(87) PCT Pub. No.: WO2009/108484
PCT Pub. Date: Sep. 3, 2009

(65) Prior Publication Data
US 2010/0324264 A1    Dec. 23, 2010

Related U.S. Application Data

(60) Provisional application No. 61/032,256, filed on Feb. 28, 2008.

(51) Int. Cl.
*C07C 31/18* (2006.01)
*C08G 63/02* (2006.01)

(52) U.S. Cl. .......................... 568/852; 528/272
(58) Field of Classification Search .............. None
See application file for complete search history.

(56) References Cited

FOREIGN PATENT DOCUMENTS
WO    2006/030291       3/2006
WO    2006030291   *   3/2006

OTHER PUBLICATIONS

Indrevoll et al., Biooroganic & Medicinal Chemistry Letters, vol. 16, No. 24, 2006, pp. 6190-6193.*
Idrevoll B et al: "NC-100717: A Versatile RGD Peptide Scaffold for Angiogenesis Imaging" Bioorganic & Medicinal Chemistry Letters, Pergamon, Elsevier Science, GB, vol. 16, No. 24, Dec. 15, 2006, pp. 6190-6193.
PCT/US2009/033620 ISRWO Dated May 25, 2009.

* cited by examiner

*Primary Examiner* — Karl J Puttlitz
(74) *Attorney, Agent, or Firm* — Yonggang Ji

(57) ABSTRACT

The present invention provides novel synthesis's for obtaining a protecting group aminoxy PEG-6 linker from cost effective, and readily available starting materials and chemicals or modified polyethylene glycols. More specifically, a novel synthesis of obtaining a modified Boc-protected aminoxy PEG-6 linker was achieved so that said linker may be attached to a vector such as a peptide based fragment.

20 Claims, 2 Drawing Sheets 23-(Boc-aminooxyacetyl-amino)-5-oxo-6-aza-3,9,12,15,18,21-hexaoxatriconsanioc acid 1,11-dihydroxy-3,6,8-trioxa-undecane 11-O-tosyl-3,6,9-trioxa-1-hydroxy-undecane N-(3,6,9-trioxa-11-hydroxy-undecane)-phthalimide 11-amino-3,6,9-trioxa-hydroxy-undecane 17-hydroxy-3,9,12,15-tetraoxa-6-aza-5-oxo-heptadecanoic acid (Boc-aminooxy) acetic acid (Boc-aminooxy) acetic anhydride

FIG.1A

| | |
|---|---|
| ![structure] 5-N-(Boc-aminooxy-acetamide)-3-oxa-1-hydroxypentane | |
| ![structure] N-(Boc-aminooxy-acetamide)-3-oxa-1-(O-tosyl)pentane | |
| ![structure] p-toluene sulfonylchloride | |
| ![structure] Potassium phtalimide | |
| H$_2$NNH$_2$ Hydrazine | |
| ![structure] diglycolic anhydride | |
| ![structure] 2(2-aminoethyl)ethanol | |
| Base to be used in final step: LDA Lithium diisopropylamine | |
| Reagents: (only those directly involved in reaction, bases, solvent, ect. included) | |

SYNTHESIS OF A PEG-6 MOIETY FROM COMMERCIAL LOW-COST CHEMICALS

This application is a filing under 35 U.S.C. 371 of international application number PCT/US2009/033620, filed Feb. 10, 2009, which claims priority to U.S. Application No. 61/032,256 filed Feb. 28, 2008, the entire disclosure of which is hereby incorporated by reference.

FIELD OF THE INVENTION

The present invention provides novel synthesis's for obtaining an aminoxy PEGylated linker from either cost effective, and readily available starting materials and chemicals or modified polyethylene glycols. More specifically, novel synthesis's of obtaining a modified Boc-protected aminoxy PEG-6 linker were achieved so that said linker may be attached to a vector such as a peptide based fragment.

BACKGROUND OF THE INVENTION

The preparation of biomolecules, such as peptides or oligonucleotides, and other organic compounds on a solid matrix is better performed using bifunctional spacer molecules known as linkers. One of the two reactive functionalities of a linker is permanently attached to a suitably functionalized resin, most often through a stable amide bond, while the growing molecule is temporarily linked at the other reactive position of the linker.

Although the majority of linkers rely on acidolysis for the release of the final molecule from the support, the use of different mechanisms (e.g. photolysis, fluoridolysis, and base-catalyzed Beta-elimination) has been exploited for the final cleavage.

Additionally biologically active molecules that selectively interact with specific cell types are useful for the delivery of radioactivity to target tissues. For example, radiolabelled peptides have significant potential for the delivery of radionuclides to tumours, infarcts, and infected tissues for diagnostic imaging and radiotherapy. $^{18}F$, with its half-life of approximately 110 minutes, is the positron-emitting nuclide of choice for many receptor imaging studies. Therefore, $^{18}F$-labelled bioactive peptides have great clinical potential because of their utility in PET to quantitatively detect and characterise a wide variety of diseases.

New blood vessels can be formed by two different mechanisms: vasculogenesis or angiogenesis. Angiogenesis is the formation of new blood vessels by branching from existing vessels. The primary stimulus for this process may be an inadequate supply of nutrients and oxygen (hypoxia) to cells in a tissue. The cells may respond by secreting angiogenic factors, of which there are many; one example, which is frequently referred to, is vascular endothelial growth factor (VEGF). These factors initiate the secretion of proteolytic enzymes that break down the proteins of the basement membrane, as well as inhibitors that limit the action of these potentially harmful enzymes. The other prominent effect of angiogenic factors is to cause endothelial cells to migrate and divide. Endothelial cells that are attached to the basement membrane, which forms a continuous sheet around blood vessels on the contralumenal side, do not undergo mitosis. The combined effect of loss of attachment and signals from the receptors for angiogenic factors is to cause the endothelial cells to move, multiply, and rearrange themselves, and finally to synthesise a basement membrane around the new vessels.

Angiogenesis is prominent in the growth and remodelling of tissues, including wound healing and inflammatory processes. Tumours must initiate angiogenesis when they reach millimeter size in order to keep up their rate of growth. Angiogenesis is accompanied by characteristic changes in endothelial cells and their environment. The surface of these cells is remodelled in preparation for migration, and cryptic structures are exposed where the basement membrane is degraded, in addition to the variety of proteins which are involved in effecting and controlling proteolysis. In the case of tumors, the resulting network of blood vessels is usually disorganised, with the formation of sharp kinks and also arteriovenous shunts. Inhibition of angiogenesis is also considered to be a promising strategy for antitumour therapy. The transformations accompanying angiogenesis are also very promising for diagnosis, one example being malignant disease, but the concept also shows great promise in inflammation and a variety of inflammation-related diseases, including atherosclerosis, the macrophages of early atherosclerotic lesions being potential sources of angiogenic factors.

Many ligands involved in cell adhesion contain the tripeptide sequence arginine-glycine-aspartic acid (ROD). The RGD sequence appears to act as a primary recognition site between the ligands presenting this sequence and receptors on the surface of cells. It is generally believed that secondary interactions between the ligand and receptor enhance the specificity of the interaction. These secondary interactions might take place between moieties of the ligand and receptor that are immediately adjacent to the ROD sequence or at sites that are distant from the ROD sequence.

The efficient targeting and imaging of integrin receptors associated with angiogenesis in vivo demands therefore a selective, high affinity RGD based vector that is chemically robust and stable. Furthermore, the route of excretion is an important factor when designing imaging agents in order to reduce problems with background.

WO 06/030291 relates to the use of peptide-based compounds as targeting vectors that bind to receptors associated with angiogenesis. Additionally, WO 2006/030291 describes peptide-based compounds having utility for diagnostic imaging which may be prepared rapidly. The present invention describes novel synthesis's of obtaining a modified Boc-protected aminoxy, $-COOCH(CH_3)_3$, PEG-6 linker. This PEG-6 linker can then be attached to a peptide based fragment to form a Boc-protected aminoxy peptide based compound. Thereafter the Boc-protected aminoxy peptide based compound is synthesized to obtain a radiolabelled peptide based compound that can be used in angiogenesis.

Discussion or citation of a reference herein shall not be construed as an admission that such reference is prior art to the present invention

SUMMARY OF THE INVENTION

The present invention depicts cost effective, and readily available starting materials and chemicals in an efficient method of preparing a PEG-6 linker with various protecting groups such as a modified Boc-protected aminoxy group, $-COOCH(CH_3)_3$, attached to one end of the linker. The present invention also depicts a novel synthesis for obtaining a PEG-6 linker by synthesizing modified polyethylene glycols.

The term "modified" used herein means a molecule that has been modified with a functional group which enables this molecule to be attached to a peptide based fragment.

Nuclear magnetic resonance spectroscopy (NMR), mass spectroscopy (MS) and HPLC-MS (high performance liquid chromatography (HPLC) in combination with MS) were utilized for identifying the intermediates in the claimed novel method of obtaining a PEG-6 linker with various protecting groups such as a modified Boc-protected aminoxy group attachment.

The current invention synthetic steps were all carried out with cost effective, and readily available starting materials and chemicals. An important advantage of using this method to prepare a PEG-6 linker with any of the below described protecting groups such as a modified Boc-protected aminoxy group attachment is that when used in combination none of the structures identified in the reaction steps are unstable. All the structures identified in the reaction steps are easily reproducible.

BRIEF DESCRIPTION OF THE DRAWINGS

FIGS. 1A and B depicts key selected structures and structure names of a linker and intermediates for making the linker, and starting materials.

DETAILED DESCRIPTION OF THE INVENTION

In preparing angiogenesis radiolabelled products, an important building block in the synthesis of obtaining a radiolabelled peptide based compound is identifying a reliable and efficient linker. In the present invention, even though there is no commercial available reagent for the PEG-6 linker, a short and convenient synthesis from commercial cost-effective and available reagents are disclosed herein.

There are advantages for using the claimed synthesis to obtain the claimed PEG-6 linker. One advantage is that the claimed synthesis is a quick process for obtaining the PEG-6 linker. Another advantage is the convenient synthesis used wherein the reagents are widely commercially available and are cost effective chemicals. More specifically, using linker A or 1, disclosed herein, for large scale production is advantageous from a cost perspective point when using starting compounds such as compound B or 2, respectively. For example, if one were to begin a reaction for making linker A or 1, one would not start with disclosed compound E or 5 since this compound is very expensive and much more difficult to isolate. It would be much more cost-effective, especially on a large scale production, to use compound B or 2 as a starting compound described herein.

The present invention also relates to a novel synthesis for obtaining a PEG-6 linker by synthesizing modified polyethylene glycols.

There are several advantages for synthesizing modified polyethylene glycols. to obtain the claimed PEG-6 linker.

One advantage is that the claimed synthesis is a short and fast process for obtaining the PEG-6 moiety. The convenient synthesis used herein can be carried out in one-day making it possible to produce the PEG-6 moiety in under two weeks.

A PEG 6 defined herein is a PEG (polyethylene glycol) consisting of a chain of six individual ethylene glycols.

As mentioned earlier, the PEG-6 modified Boc-protected aminoxy linker obtained herein, compound (I), can be attached to a vector. Specifically, that vector can be a peptide based fragment, compound (II), that forms a Boc-protected aminoxy peptide based compound, compound (III). Thereafter the Boc-protected aminoxy peptide based compound is synthesized to obtain a radiolabelled peptide based compound, for example, an $^{18}$F-based peptide compound, as shown in compound (IV), that can be used in angiogenesis.

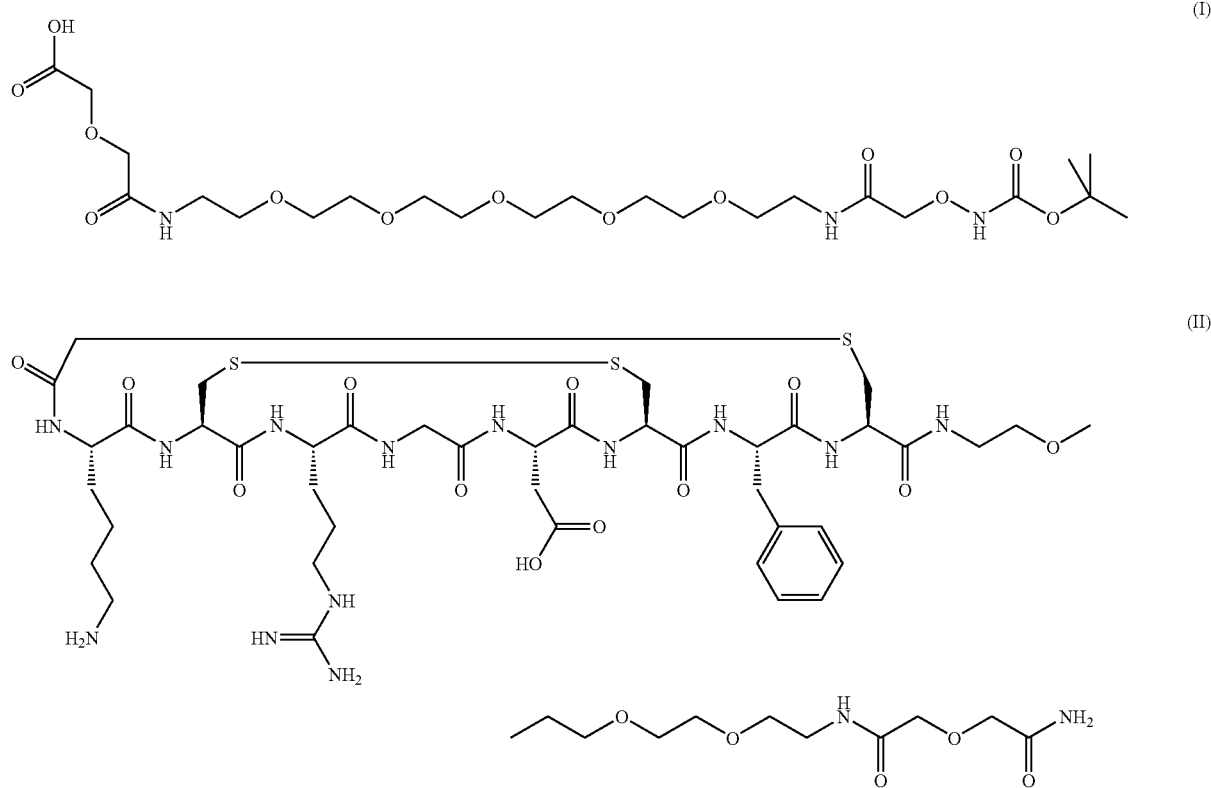

(III)

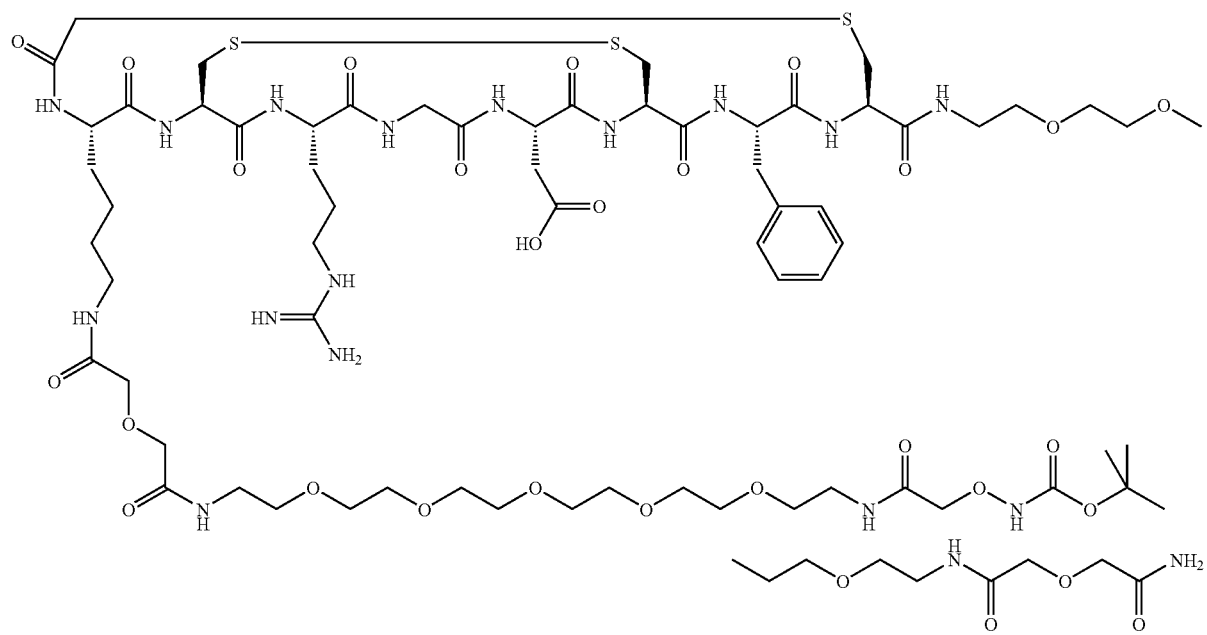

(IV)

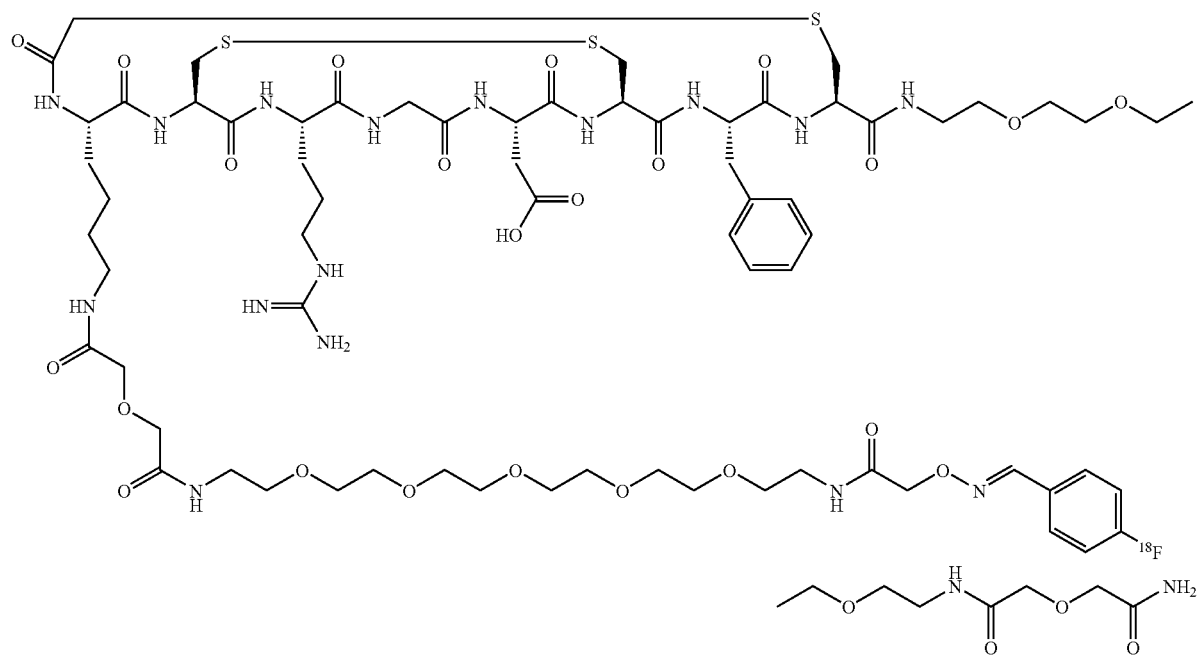

The term linker as used herein means a moiety that links together at least two other moieties, such as a vector and a reporter. The use of linker groups with different lipophilicities and or charge can significantly change the in vivo pharmacokinetics of a peptide to suit the diagnostic need. A wide variety of linkers may be used, including biodegradable linkers and biopolymers. The linker is at its simplest a bond between the vector and the aminoxy group. More generally, the linker will provide a mono- or multi-molecular skeleton, e.g. a linear, cyclic, or branched skeleton. The linker may further have the role to distance the vector from the reporter. The linker described herein specifically comprises macromolecular structures such as dextran and preferably poly(ethyleneglycols), referred to as PEGs. Linkers including a PEG moiety have been found to slow blood clearance which is desirable in some circumstances. The linker may be derived from glutaric and/or succinic acid and/or a polyethyleneglycol based moiety.

All molecules that have a PEG center moiety of different lengths and a protected aminoxy acetic acid on one side and a spacer connected as an amide to other terminal end of the PEG moiety can be synthesized following the described synthetic protocol accordingly in preparing formula (I) without the use of an azide, the anion with the formula $N_3^-$.

Additionally, the synthetic protocol described below enables formation of PEG moieties of different lengths, i.e. the number of ethylene glycols coupled in series.

A vector is defined herein as a fragment of a compound or moiety having affinity for a receptor molecule, preferably a peptidic species or more preferably an angiogenesis targeting species such as an RGD peptide. A specific example of a vector used herein is an Arg-Gly-Asp peptide or an analogue thereof. An example of such a vector used herein comprises the fragment

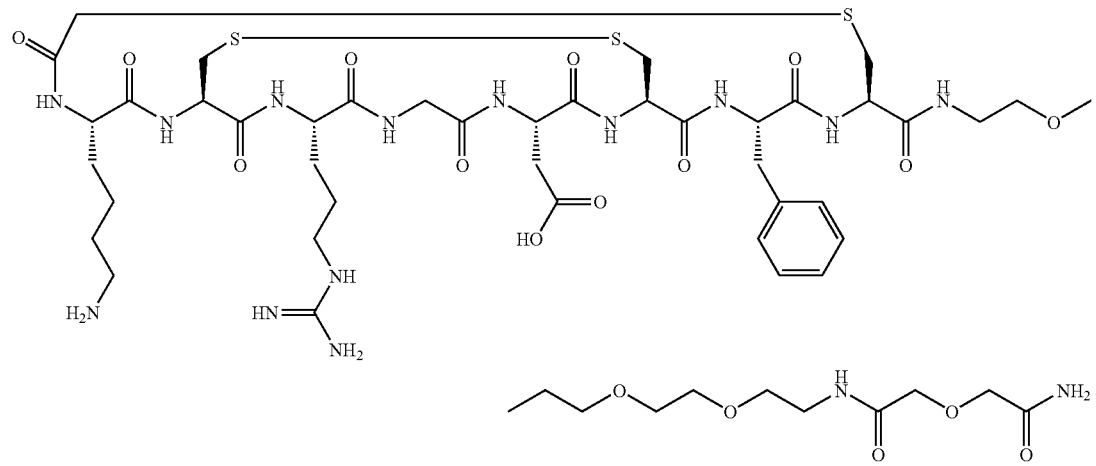

One embodiment of the present invention depicts a method for preparing a linker. More specifically a protecting group ("PG") such as a Boc-protected aminoxy linker, formula (A), can be prepared according to the following method:

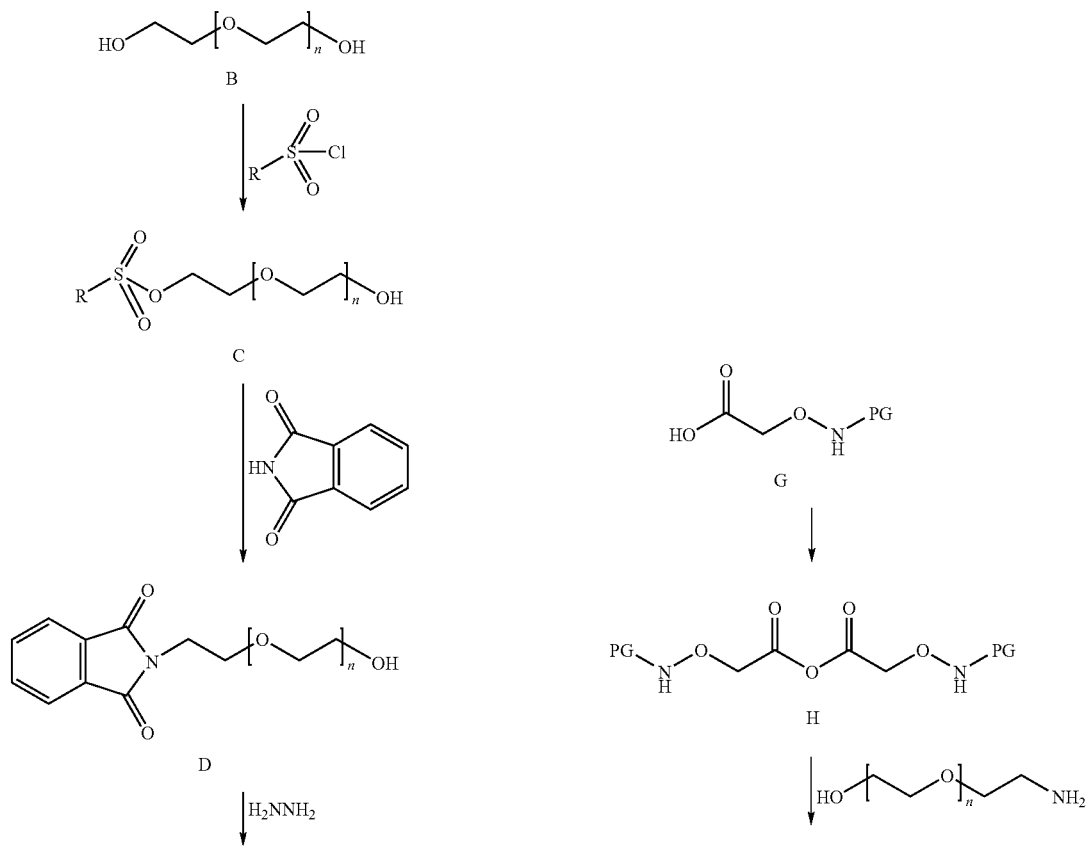

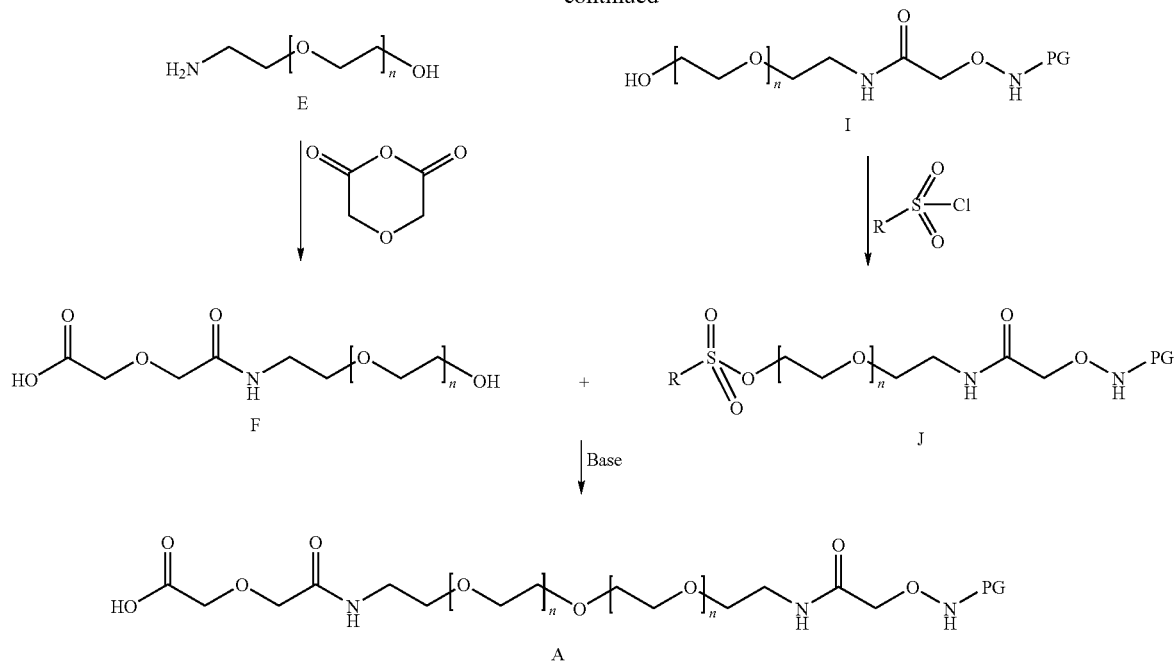

wherein R denotes one of the following structures

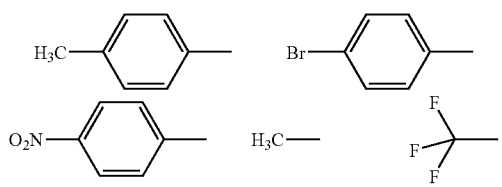

and
wherein PG can be either a carbamate of the form

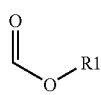

where R1 is alkyl or aryl and more preferably R1=9-fluorenylmethyl meaning that PG is 9-fluorenylmethoxycarbonyl and most preferably R1=tert-butyl meaning that PG is Boc, t-butoxycarbonyl (—COOCH(CH₃)).
or wherein PG denotes

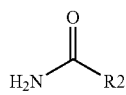

where R2=alkyl or aryl and more preferably R2=H meaning that PG is formyl or R2 is a methyl meaning that PG is acetyl and most preferably where R2=phenyl meaning that PG is benzoyl
or further wherein PG can be alkyl or aryl and more preferable allyl or most preferable benzyl.
and n denotes 1-19.

It is important to note here that the key intermediates are D to E and H to I of this method. The term key is defined herein as crucial and necessary to make said linker.

The process time for making 1 kilogram of linker A beginning with intermediates B and G can be in the range from about 1 week to about 5 weeks. Furthermore, if intermediates F and J are made parallel to each other than the total synthesis time to make 1 kilogram of linker A will take between 3 to 4 weeks. The last step, coupling of F with J, followed by purification by HPLC (high preformance liquid chromotography) does not take up more than 1 week to complete. The novel synthesis disclosed herein is not only shorter in time compared with other alternative synthesis steps but it is also much more commerically viable to users.

Another embodiment of the present invention depicts a method for preparing a linker of formula (I), comprising the following reactions:

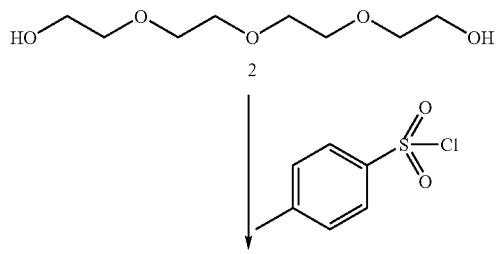

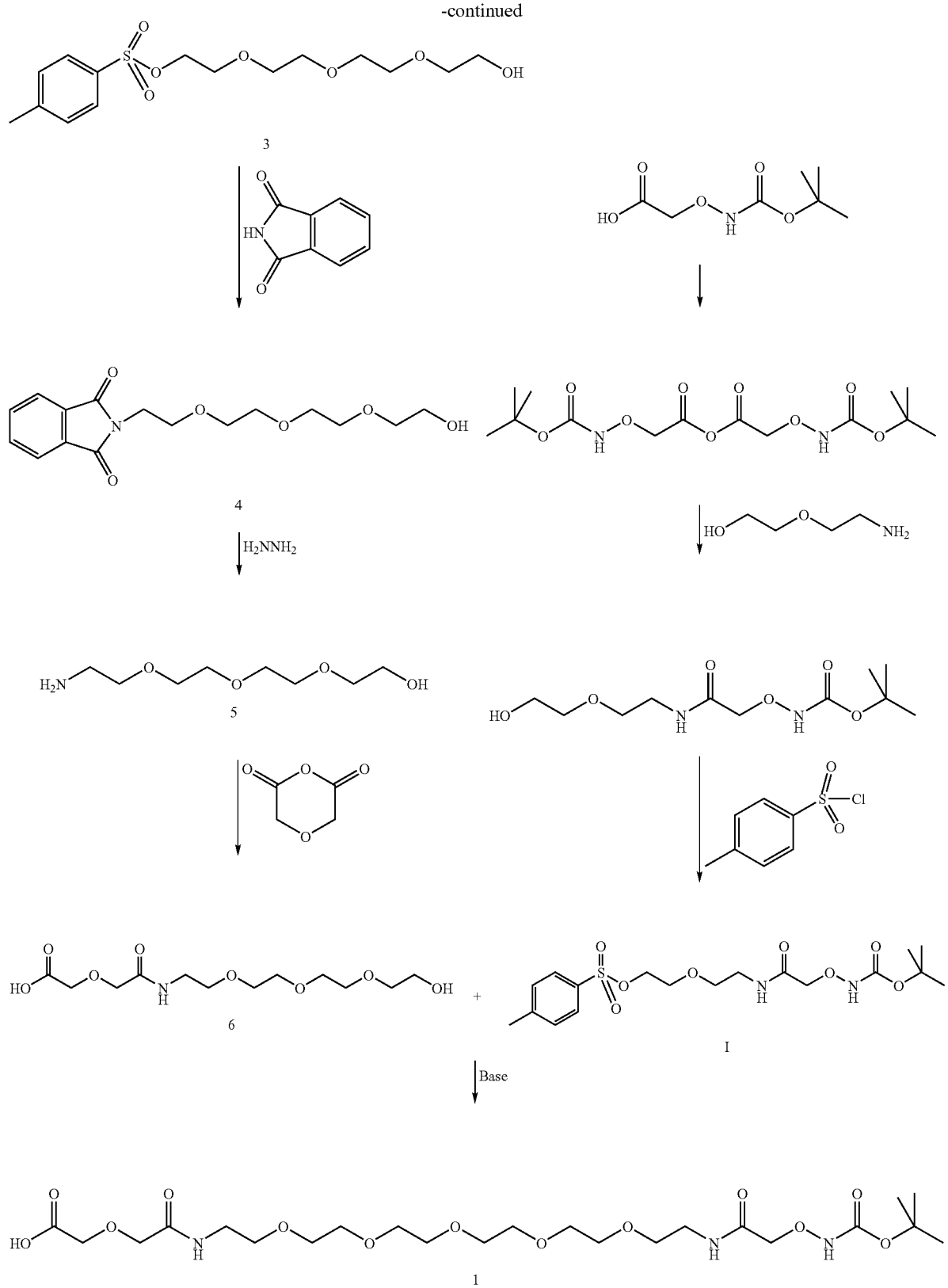
wherein the formula of linker (1) is a Boc-protected aminoxy linker and the base combining 6 and 10 is lithium diisopropylamine.
Yet another embodiment of the invention presents a method wherein a vector such as a peptide fragment, compound (II):

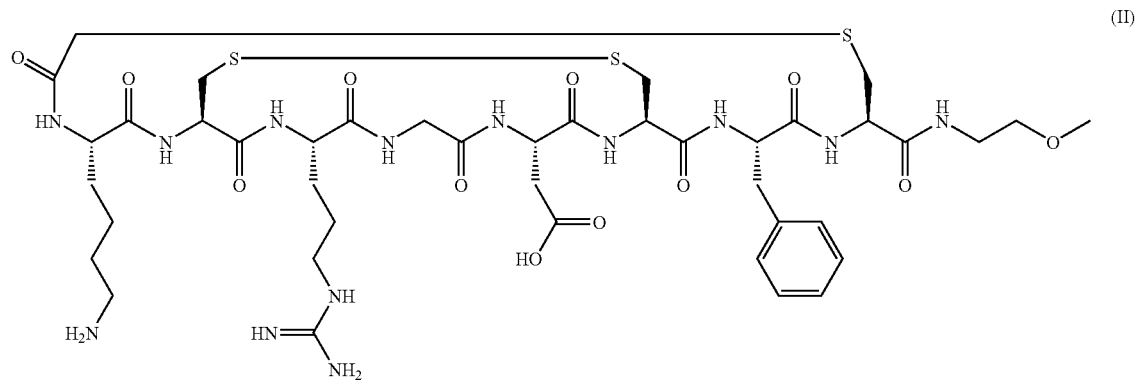
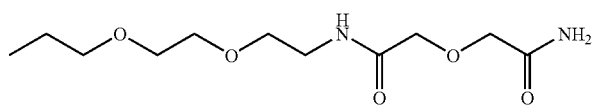
is connected to the linker of formula (A) to form compound (III):
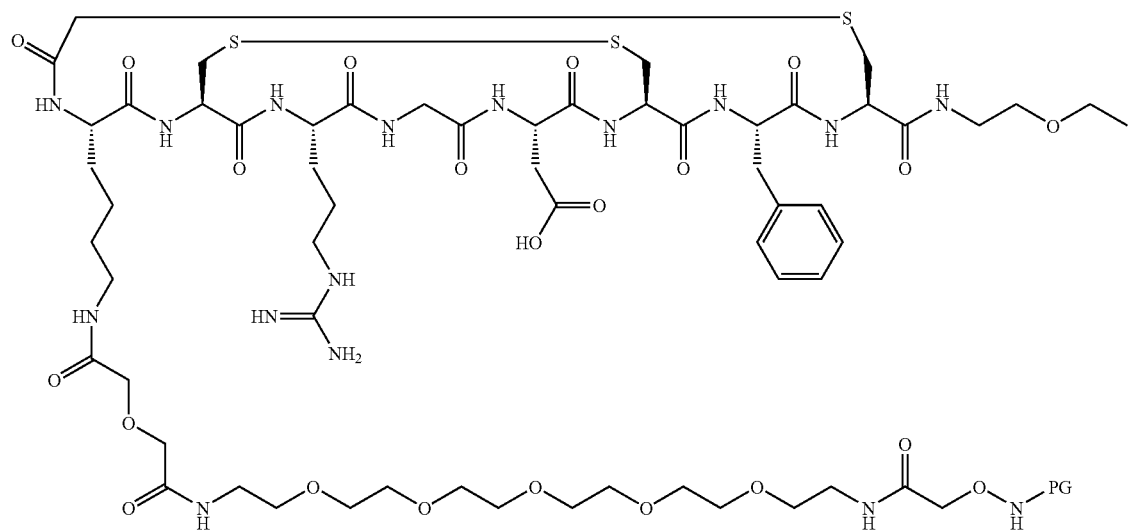
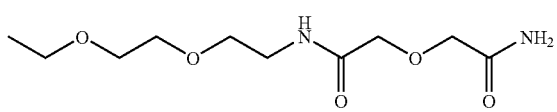

and thereafter compound (III) reacts with 4-$^{18}$F fluorobenzene to form compound (IV)
(IV)
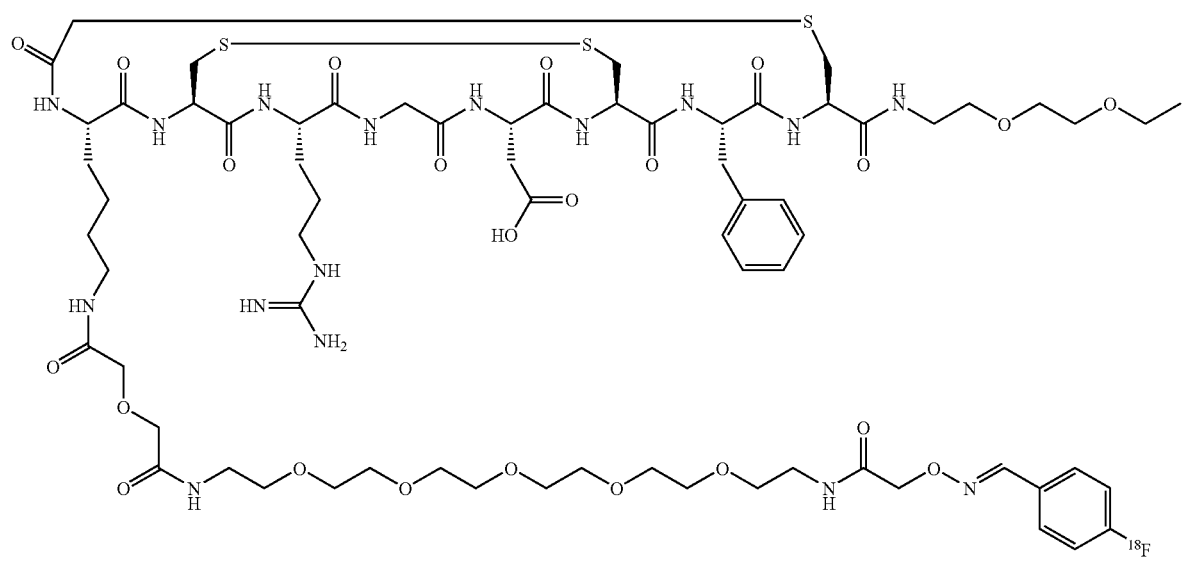
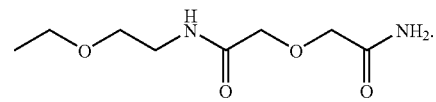
Yet another embodiment of the invention presents a method wherein a vector such as a peptide fragment, compound (II):
(II)
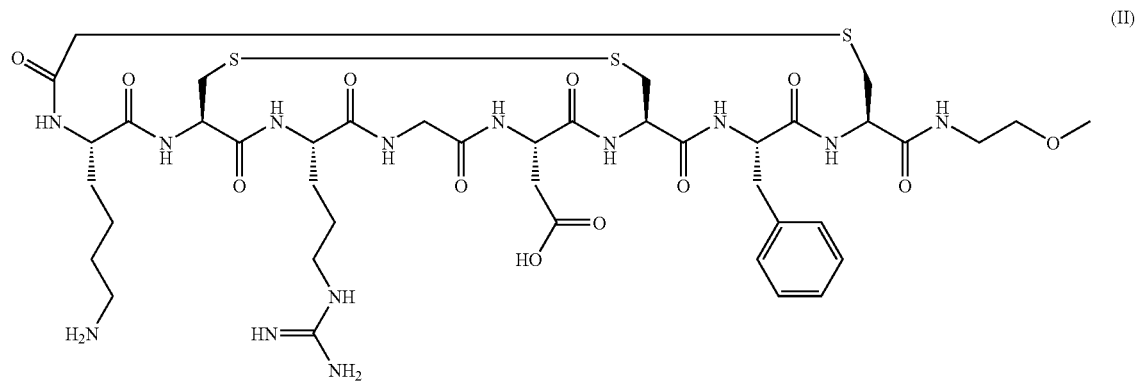
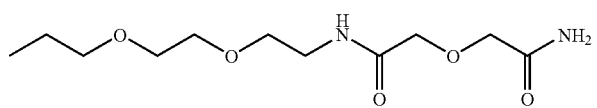

connects with a the linker of formula (I) to form compound (IIIa):
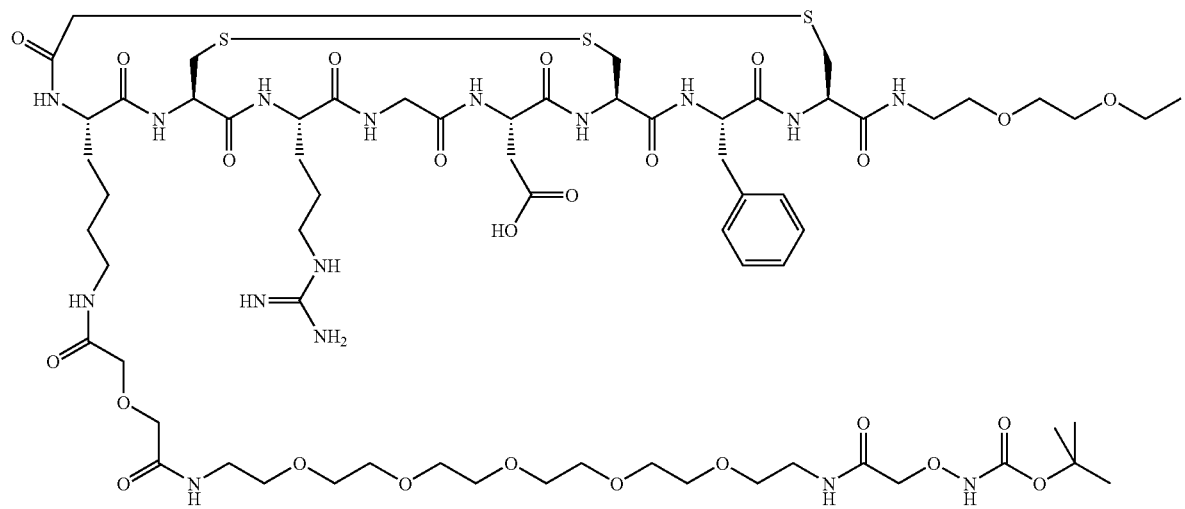
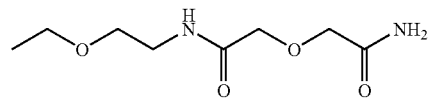
and thereafter compound (IIIa) reacts with 4-$^{18}$F fluorobenzene to form compound (IV)
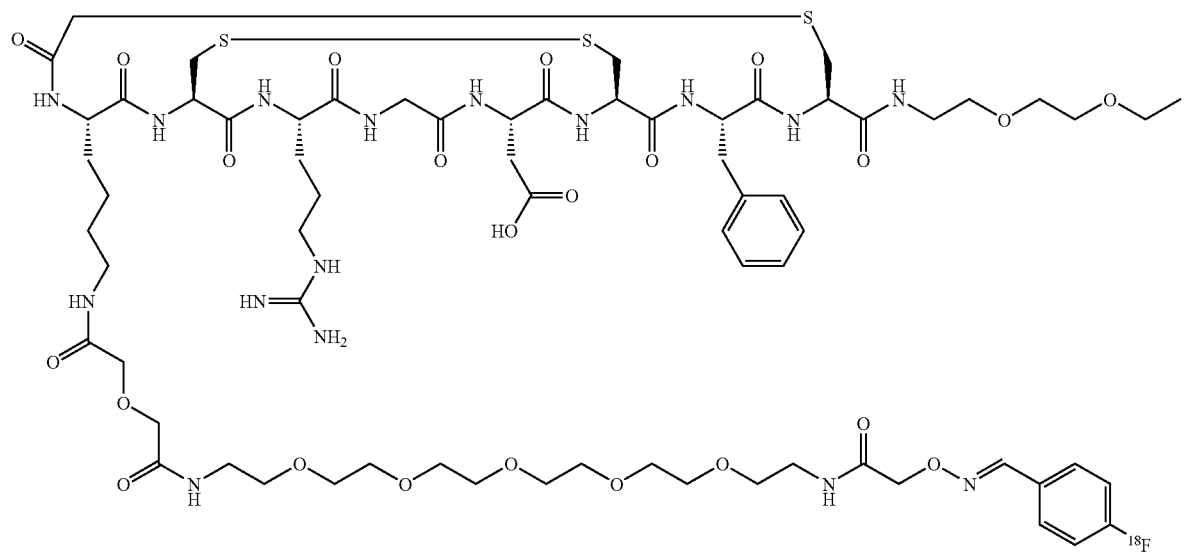
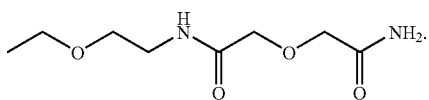

A further embodiment of the invention shows the method to obtaining formula (A) from the following reaction:

Another embodiment of the present invention according to the above reaction of obtaining formula (A) is dissolving

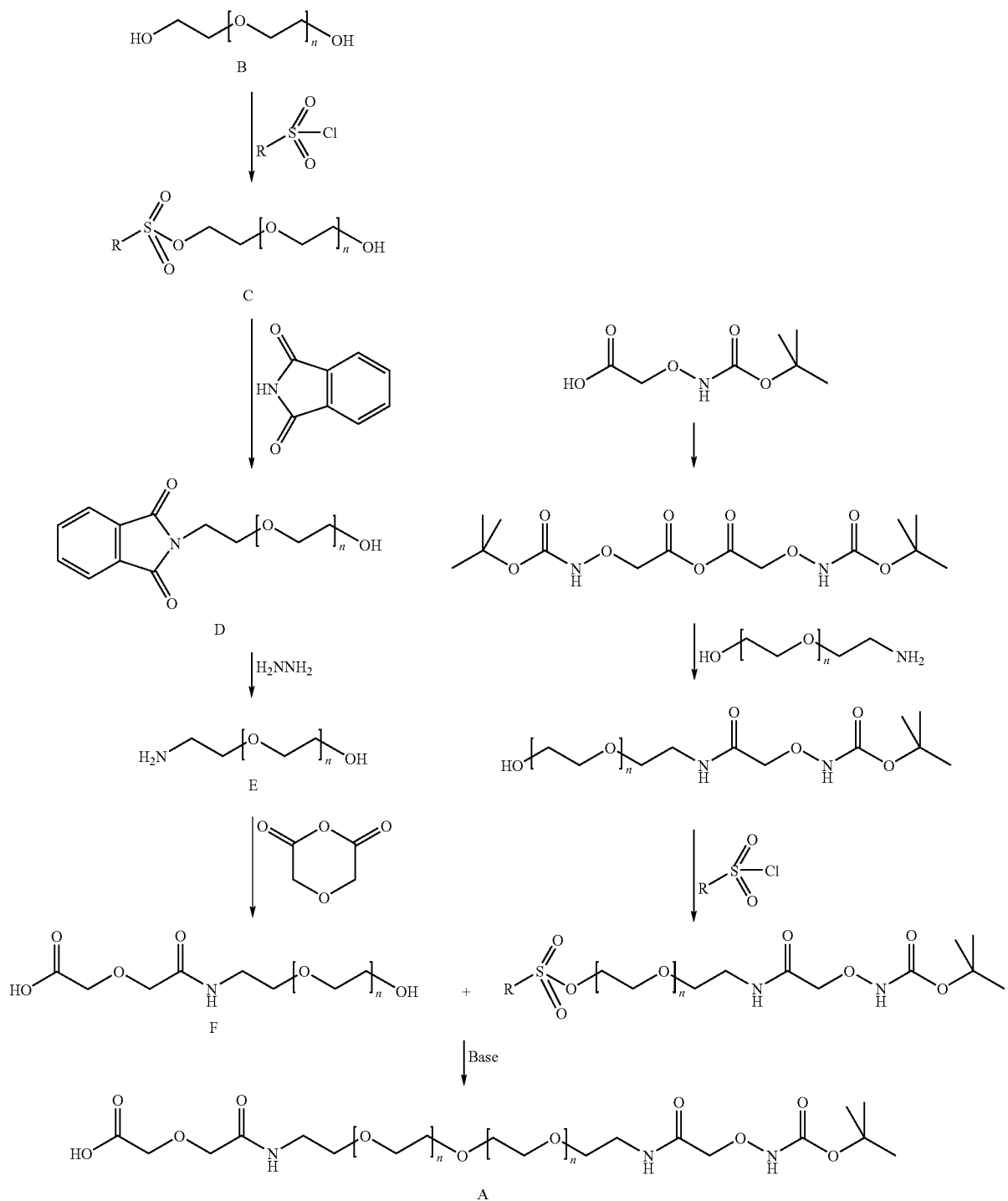

wherein p-toluene sulfonylchloride is used to react with 1,11-dihydroxy-3,6,8-trioxa-undecane, (B). These two compounds were mixed together at a temperature in the range of about 15° C. to about 27° C. over about 6 hours to about 15 hours to form 11-O-tosyl-3,6,9-trioxa-1-hydroxy-undecane, (C) further wherein the preferred temperature is about 22° C. and the preferred time is about 8 hours.

11-O-tosyl-3,6,9-trioxa-1-hydroxy-undecane, (C), in dimethyl formamide and potassium phthalimide was stirred into (C) for about 6 hours to about 15 hours at a temperature range of about 70° C. to about 100° C. to form N-(3,6,9-trioxa-11-hydroxy-undecane)-phthalimide, (D).

A further embodiment of the invention according to the above reaction of obtaining formula (A) is dissolving (D) in tetrahydrofuran at a temperature range from about 30° C. to about 70° C. to obtain purification of (D).

Yet another embodiment of the invention according to the above reaction of obtaining formula (A) is dissolving about 80 to about 120 milligrams of compound (D) in methanol and then adding hydrazine monohydrate to compound (D) and then heating compound (D) to about 30° C. to about 80° C. for about 1 to about 5 hours and then cooling the mixture to room temperature and stirring the mixture for about 6 hours to about 15 hours thus forming 11-amino-3,6,9-trioxa-hydroxy-undecane, (E).

Another embodiment of the invention according to the above reaction of obtaining formula (A) is mixing (E) with about 1.0 mole of dichloromethane, 1.0 mole of dimethyl formamide, and 1.5 moles of diglycolic anhydride and heating the mixture to a temperature range of about 30° C. to about 50° C. for about 1 to about 3 hours.

Still another embodiment of the present invention according to the above reaction of obtaining formula (A) is adjusting the pH of compound (E) to about 9 to about 15 with about 1 mole of NaOH(aq) thus forming 17-hydroxy-3,9,12,15-tetraoxa-6-aza-5-oxo-heptadecanoic acid, (F).

A further embodiment of the invention according to the above reaction of obtaining formula (A) is dissolving (Boc-aminoxy)acetic acid, (G), in acetic anhydride and heating the mixture to a temperature in the range of about 40° C. to about 70° C. for about 48 hours to about 72 hours to form (Boc-aminooxy)acetic anhydride, (H).

Still another embodiment of the invention according to the above reaction of obtaining formula (A) is dissolving formula (H in tetrahydrofuran and 2(2-aminoethyl)ethanol and then stirring the mixture at room temperature for about 2 to 4 days.

Another embodiment of the present invention according to the above reaction of obtaining formula (A) mixing formula (H) with water and adjusting a pH to about 9 to 12 with NaOH(aq) and then stirring said mixture for about 6 hours to about 15 hours to form 5-N-(Boc-aminooxy-acetamide)-3-oxa-1-hydroxypentane, (I).

Yet another embodiment of the present invention according to the above reaction of obtaining formula (A) combines formulas (F) and (J) by the base, lithium diisopropylamine.

EXAMPLES

The invention is further described in the following examples, which are in no way intended to limit the scope of the invention.

The invention is illustrated by way of examples in which the following abbreviations are used:
p: para
o: ortho
HPLC: high performance liquid chromatography
MS: Mass Spectometry
LC-MS: Liquid Chromotography/Mass Spectometry
TEG: tetraethyleneglycol
DMF: Dimethyl formamide
$^1$H-NMR: proton nuclear magnetic resonance
THF: Tetrahydrofuran
DMA: Dimethyl acetamide
hr(s): hour(s)
min(s): minute(s)
mg: milligrams
Boc: —COOCH($CH_3$)$_3$
RT: room temperature
C: temperature in Celsius
M+H$^+$: defined herein as Mass of an ion detected in mass spectrometry as the adduct between a molecule and a proton.
M+Na$^+$: defined herein as Mass of an ion detected in mass spectrometry as the adduct between a molecule and a sodium ion.
UV: ultraviolet
Synthetic Route for the Synthesis of a Boc-Protected Aminoxy Linker A synthetic route for the synthesis of a Boc-protected aminoxy linker is seen in the scheme below. MS and LS-MS were the major analytical tools used for identification of the intermediates.

All synthetic steps were carried out using relatively inexpensive and readily available starting materials and chemicals. These steps were carried out using established organic synthetic methods. None of the steps can be identified as costly or inefficient.

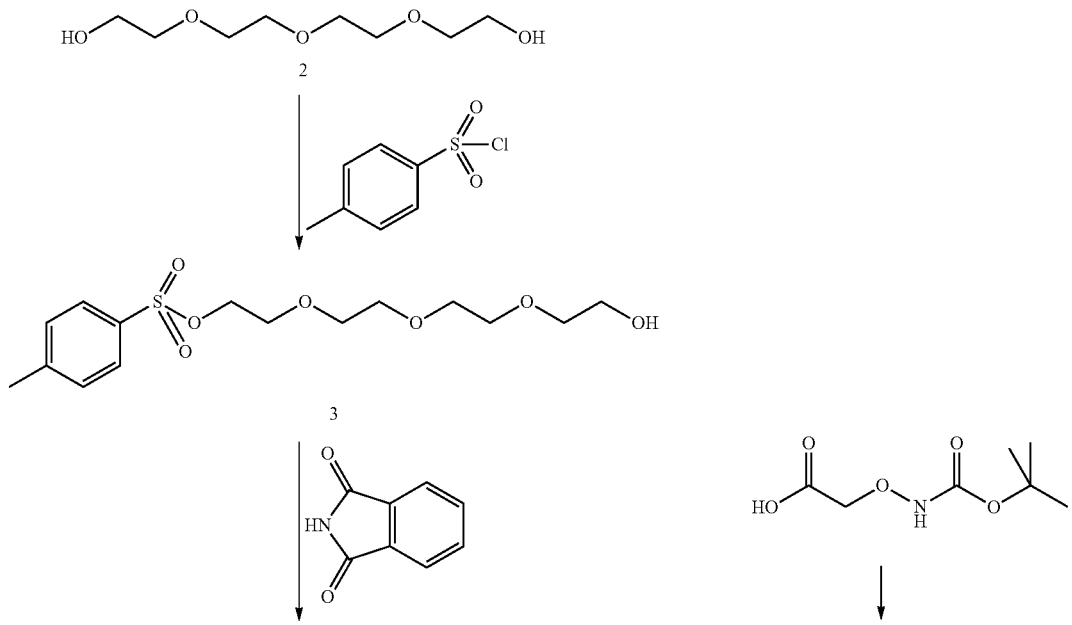

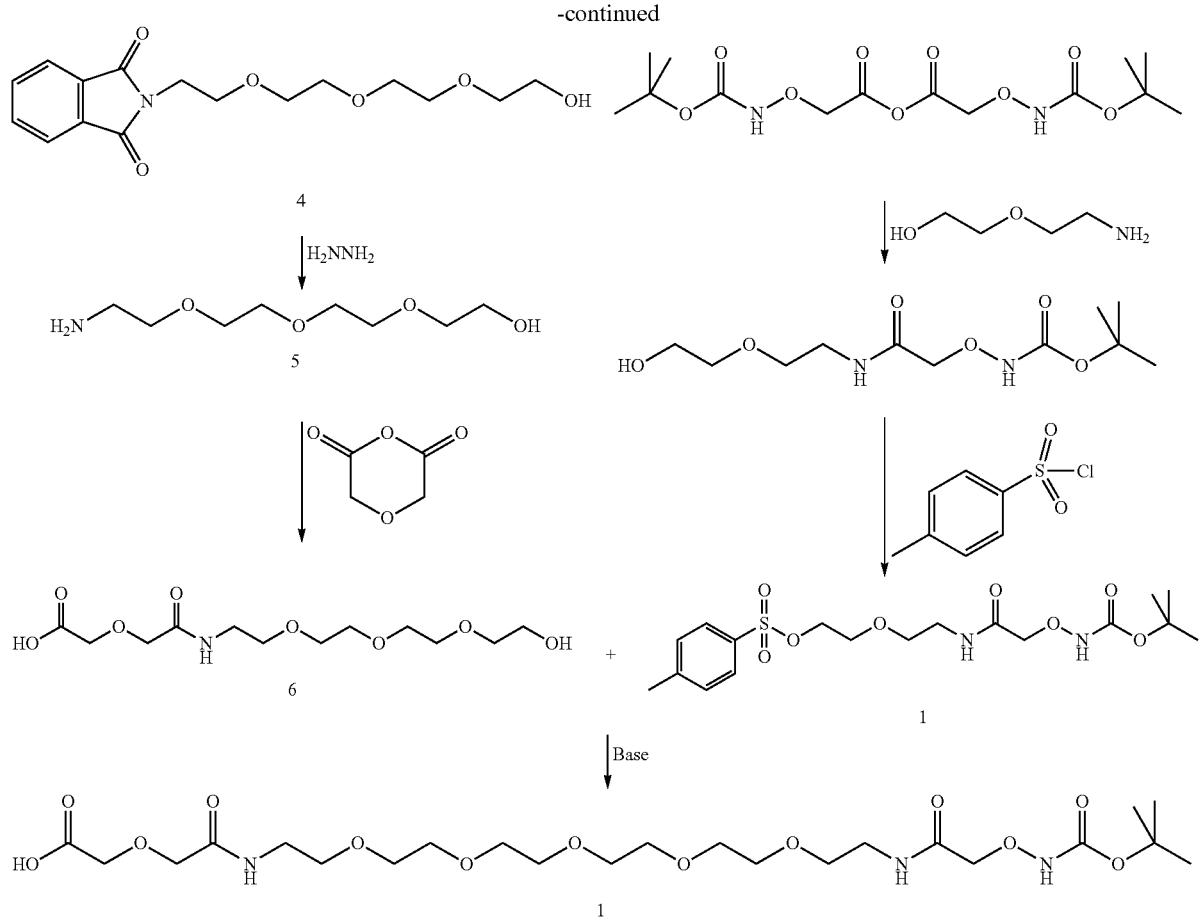

Experimental Data of Each Process Step for the Synthesis of the Boc-Protected Aminoxy Linker i. 11-O-tosyl-3,6,9-trioxa-1-hydroxy-undecane (3)

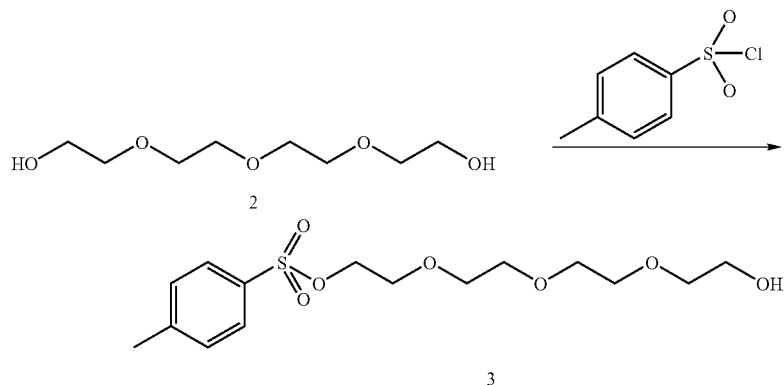

A pre-made solution of p-toluene sulfonylchloride was added dropwise over 60 min to a solution of triethylamine and 1,11-dihydroxy-3,6,9-trioxa-undecane (TEG)(2) chloroform. The reaction mixture was stirred at ambient temperature (20-23° C.) over night. The reaction mixture was thereafter filtered and the filtrate evaporated under reduced pressure. Residue was first mixed and shaken with hexane, thereafter with ethyl acetate/hexane 1:1 and finally the product was extracted from the residue by suspending the residue in ethyl acetate. The suspension was filtered and the product collected in the filtrate. The filtrate was evaporated under reduced pressure and the residue analysed by MS.

The Ms Confirmed a Mix of Unreacted, Monotosylated (M+H$^+$349.14) and Ditosylated (M+H$^+$503.15)

ii. Formation
N-(3,6,9-trioxa-11-hydroxy-undecane)-phthalimide
(4)

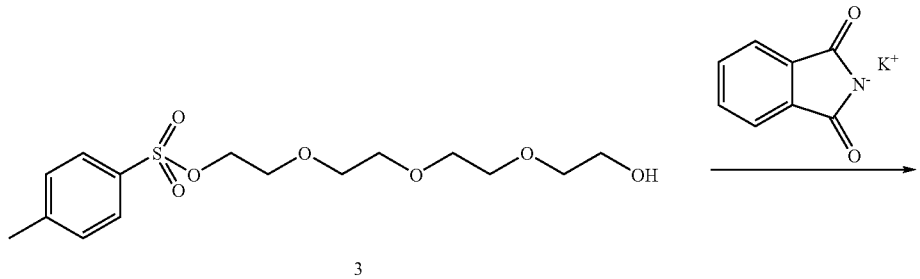

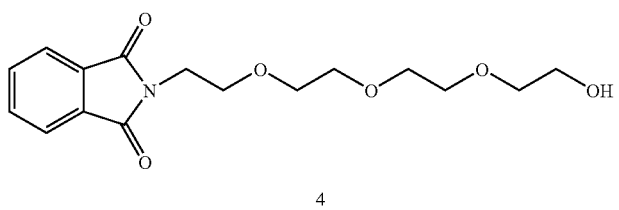

The tosylated TEG (3) from first step was dissolved in DMF and potassium phthalimide and added. The reaction mixture was stirred at 80° C. over night. The morning after the temperature was raised to 90° C. for two hours. After cooling to room temperature the mixture was filtered and the filtrate evaporated under reduced pressure. The residue was mixed with methanol and filtered and the filtrate evaporated under reduced pressure. This procedure was repeated with diethyl ether.

iii. Purification of
N-(3,6,9-trioxa-11-hydroxy-undecane)-phthalimide
(4)

The crude N-(3,6,9-trioxa-11-hydroxy-undecane)-phthalimide containing bis-N-phthalimide was dissolved in as little THF as possible. The THF solution was added drop wise to water at 40-60° C. The bisamide precipitated from water and was removed by filtration after cooling. The filtrate was evaporated under reduced pressure and the diethyl ether was added to the residue and product extracted from the solid residue into the diethyl ether. The ether was decanted and the procedure repeated once. The residue was mixed with water and extracted with 1× diethyl ether and 2× ethyl acetate. The combined ethyl acetate phases were evaporated under reduced pressure. The ether phases were combined, decanted and evaporated. The residue was dissolved in ethyl acetate and the solution was added to the product isolated from exhilarate extraction. This second ethyl acetate solution was evaporated under reduced pressure. The structure of 4 was confirmed by $^1$H-NMR. The ratio between product 4: bisimide: TEG was 86:2:12 (NMR).

iv. 11-amino-3,6,9-trioxa-hydroxy-undecane

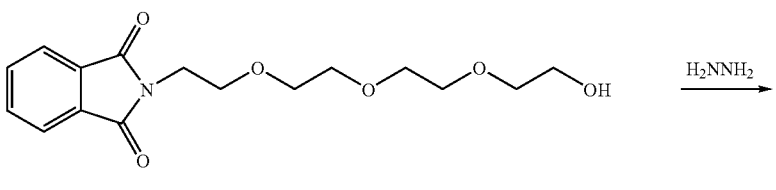

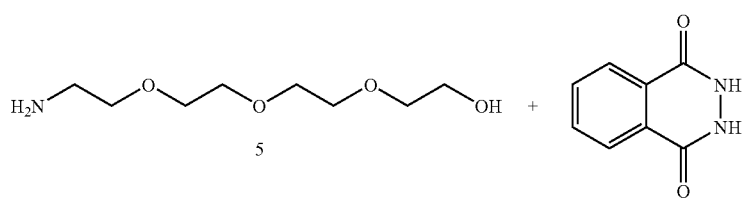

100 mg of compound 4 was dissolved in methanol and hydrazine monohydrate added. The mixture was heated to 50° C. for 3 hours, cooled to room temperature and stirred at room temperature over night.

MS confirmed desired product (M+H$^+$194.1).

v. 17-hydroxy-3,9,12,15-tetraoxa-6-aza-5-oxo-heptadecanoic acid (6)

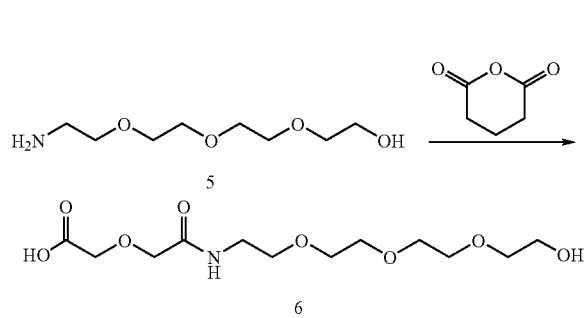

The amine 5 was mixed with dichloromethane and some DMF as co-solvent. 1.5 mole eqv. diglycolic anhydride wad added and the mixture heated to 40° C. for a couple of hours. After cooling to room temperature and stirring over weekend the reaction mixture was evaporated under reduced pressure. The residue was mixed with water and pH adjusted to pH between 11-12 with 1N NaOH$_{(aq)}$ for hydrolysis of the ester. The solution was allowed to stir over night and was thereafter acidified with HCl to pH 1-2 and evaporated under reduced pressure.

LC-MS of the residue showed a major peak with the expected masses M+H$^+$310.15 and M+Na$^+$332.13.

vi. (Boc-aminooxy)acetic anhydride (8)

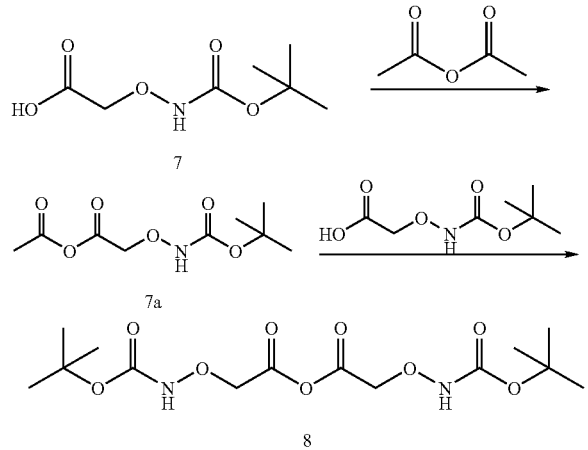

(Boc-aminooxy)acetic acid (7) was dissolved in acetic anhydride and heated to 50-60° C. over the weekend. LC-MS of the reaction mixture showed several different products including the mixed anhydride 7a and the symmetric anhydride 8.

The anhydride 7a was originally the target compound, however, 8 was found in the reaction mixture and is a better reagent than 7a for the next step (see above) since N-acylation with 7a can give two different products; N-(boc-aminooxy) acetamide as the wanted product and N-acetamide as by-product.

Structure of compound 8 was confirmed by LC-MS (M+H$^+$ 365) fragments with M+H$^+$265.1 and M+H$^+$165 indicated the loss of one and two Boc-groups.

vii. 5-N-(Boc-aminooxy-acetamide)-3-oxa-1-hydroxypentan (9)

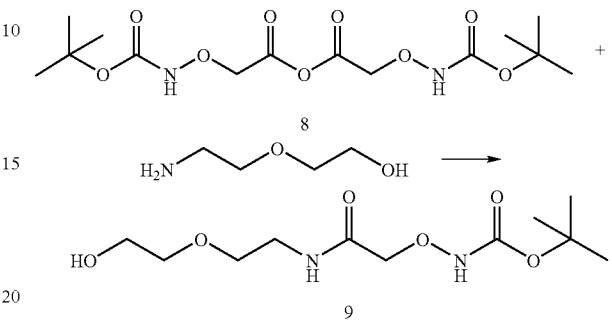

A mixture containing compound 8 was dissolved in THF and 2(2-aminoethyl)ethanol added. The reaction mixture was stirred at room temperature for 3 days. The reaction mixture was mixed with water and pH adjusted to above 10 with NaOH$_{(aq)}$ and stirred over night. The reaction mixture was added to THF and brine and extracted. The evaporated THF phase was used directly in the next step.

Product was identified using LC-MS.

viii. 5-N-(Boc-aminooxy-acetamide)-3-oxa-1-(O-tosyl)pentane(9)

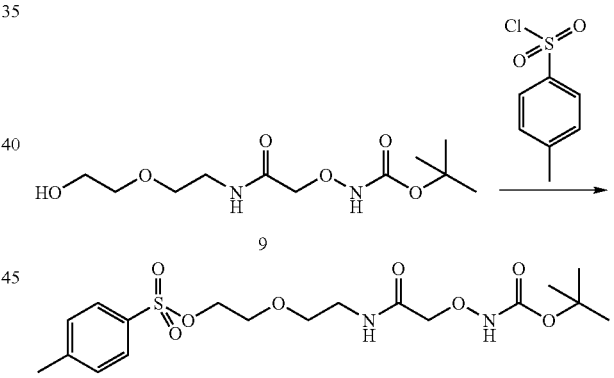

Discussion/Results

The target compound a Boc-protected aminoxy linker is to be made by coupling between intermediate 6 and 10. Results for the experiments shows that both compound 6 (4 synthetic steps) and 10 (3 synthetic steps) can be made by simple synthetic methods. Compound 10 was made in three synthetic steps without any form for purification. The ether formation using the suggested method was confirmed in experiment ix above.

An important step in the synthesis is formation of compound 9. There are several approaches to perform this. One is to make the acid halide of compound 7, however, the Boc group is not to stable during e.g. acid chlorination. One other method is to use coupling reagents. A problem using couplings reagents is the low molecular weights of product and reagents.

The formation of compound 8 might be the better solution and the formation is proved in experiment vi, see above. Tuning of this synthesis to give a relatively pure compound 8 seems to be the key for success. A follow-up on this step is done by using an in-situ made mixed anhydride between formic- and acetic acid. The higher reactivity of formyl over acetyl would give a mixed anhydride between 7 and formyl. The formyl group is less stable than acetyl and the formation of 8 should be favored if 7 is present. The anhydride 8 is regarded as the thermodynamic preferred structure over the mixed anhydrides.

SPECIFIC EMBODIMENTS, CITATION OF REFERENCES

The present invention is not to be limited in scope by specific embodiments described herein. Indeed, various modifications of the inventions in addition to those described herein will become apparent to those skilled in the art from the foregoing description and accompanying figures. Such modifications are intended to fall within the scope of the appended claims.

Various publications and patent applications are cited herein, the disclosures of which are incorporated by reference in their entireties.

What is claimed is:

1. A method for preparing a linker of formula (A), comprising the following reactions:

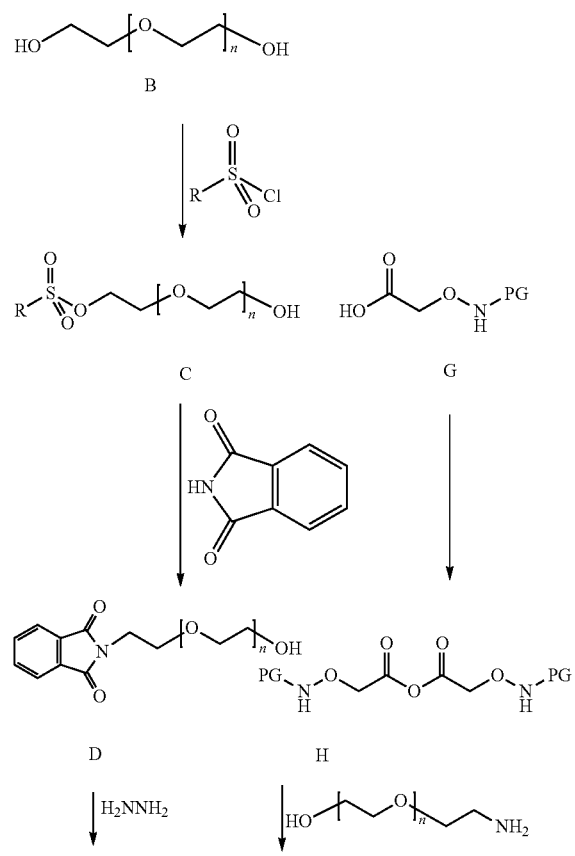

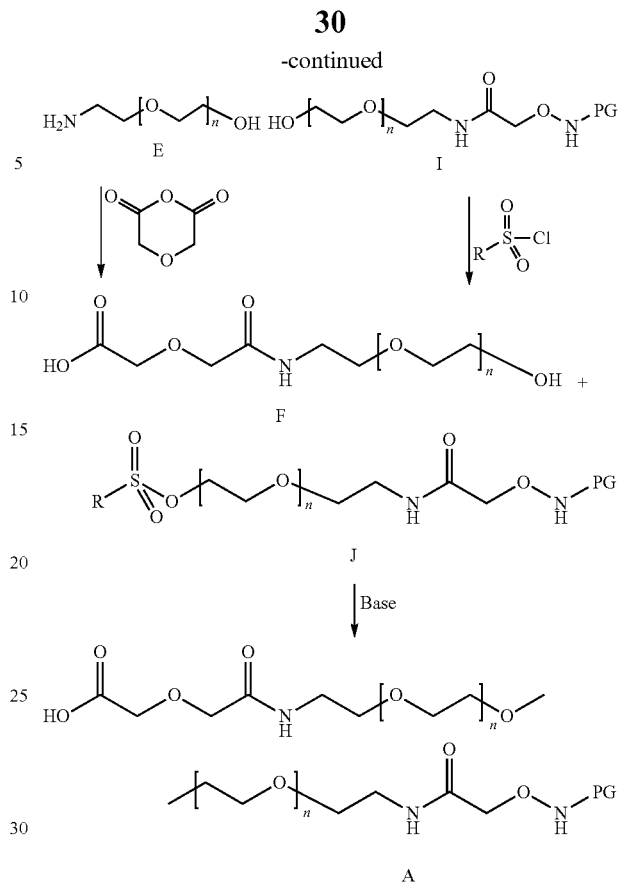

wherein R denotes one of the following structures:

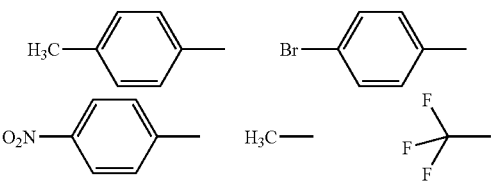

and wherein PG can be either a carbamate of the form

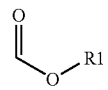

where R1 is alkyl or aryl
or wherein PG denotes

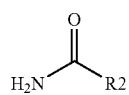

where R2=alkyl or aryl
or further wherein PG can be alkyl or aryl
and n denotes 1-19.

2. A method for preparing a linker of formula (1), comprising the following reactions:
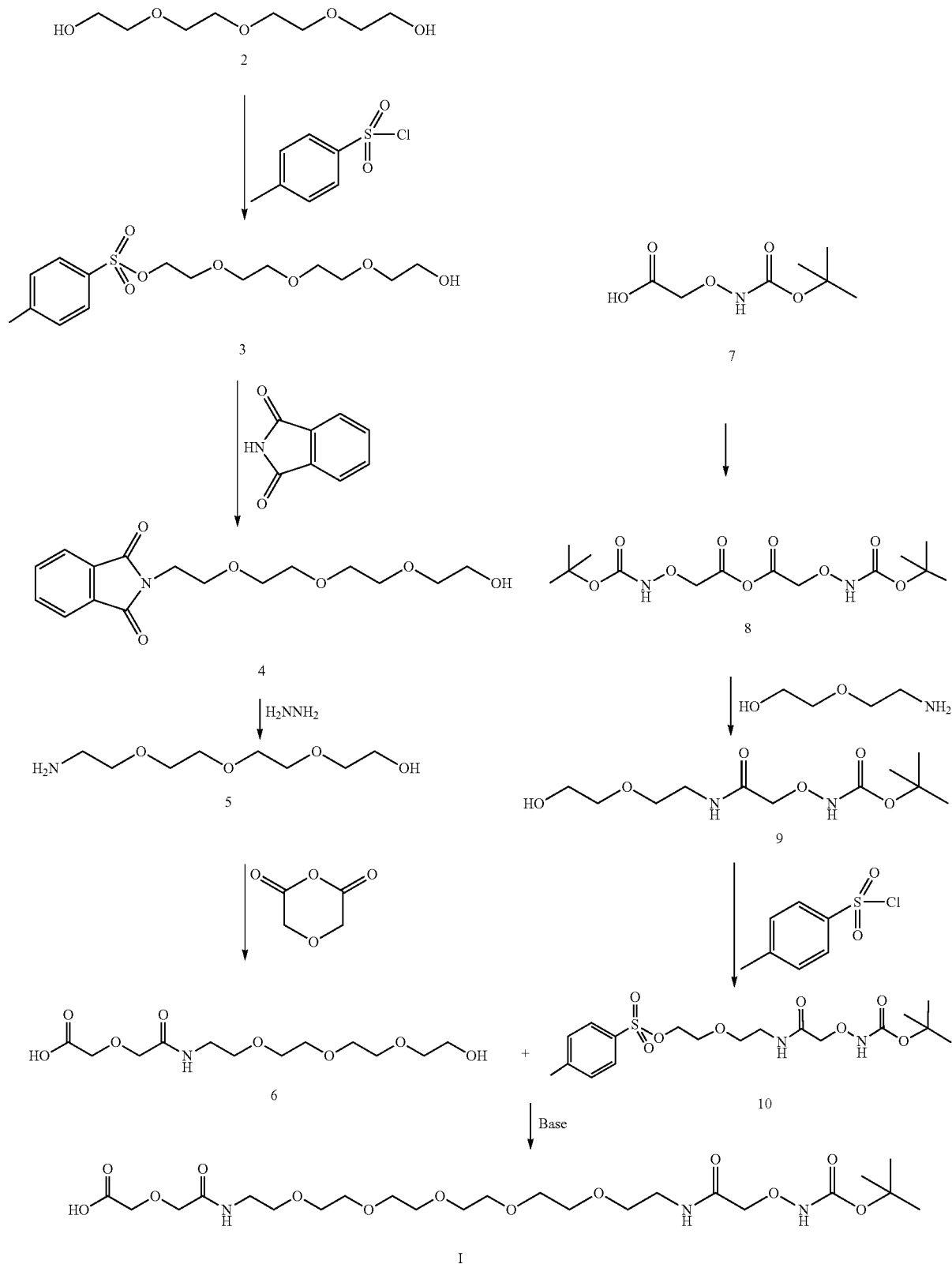
wherein the formula of linker (1) is a Boc-protected aminoxy linker.
3. A method for preparing a compound of formula (III), comprising:

(i) preparing a linker of formula (A), wherein n=2 according to the method of claim 1, and
(ii) reacting the linker of formula (A) from step (i) with compound (II):
(II)
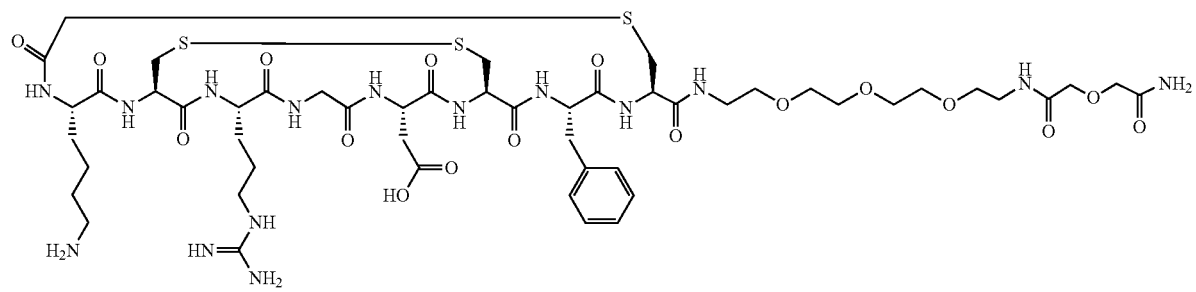
to form compound (III)
(III)
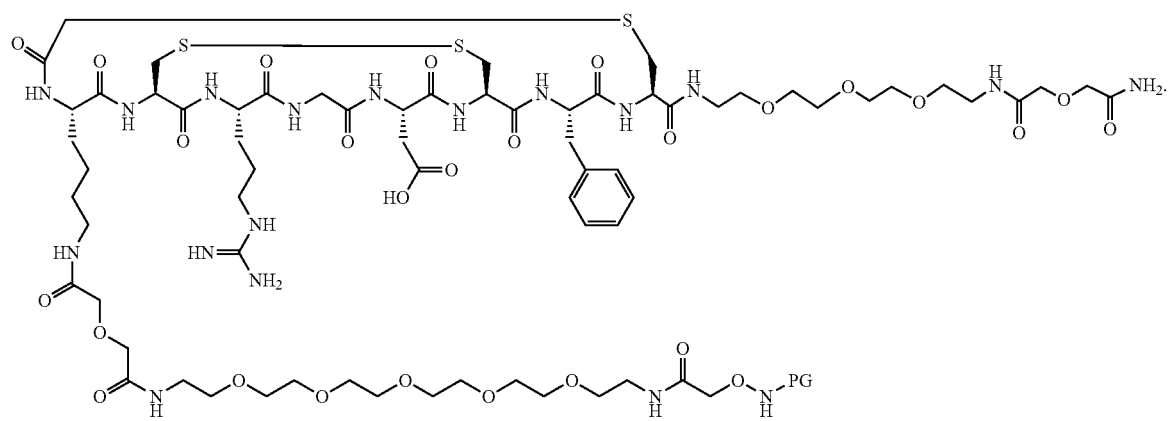
4. A method for preparing compound (IV), comprising preparing compound (III) according to the method of claim 3, and reacting compound (III):
with 4-$^{18}$F fluorobenzaldehyde to form compound (IV):
(IV)
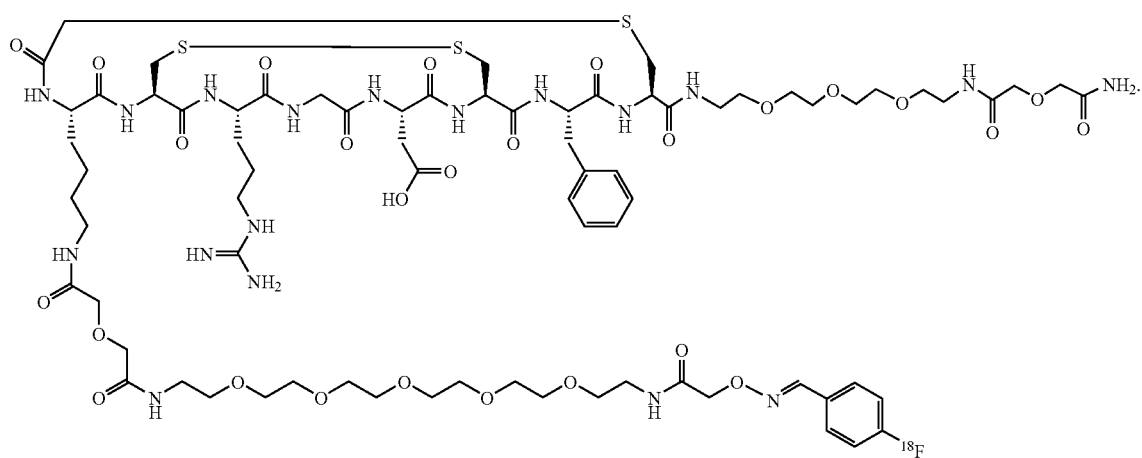

5. A method for preparing compound (IIIa), comprising preparing the linker of formula (1) according to the method of claim 2, and reacting said linker of formula (1) with compound (II):
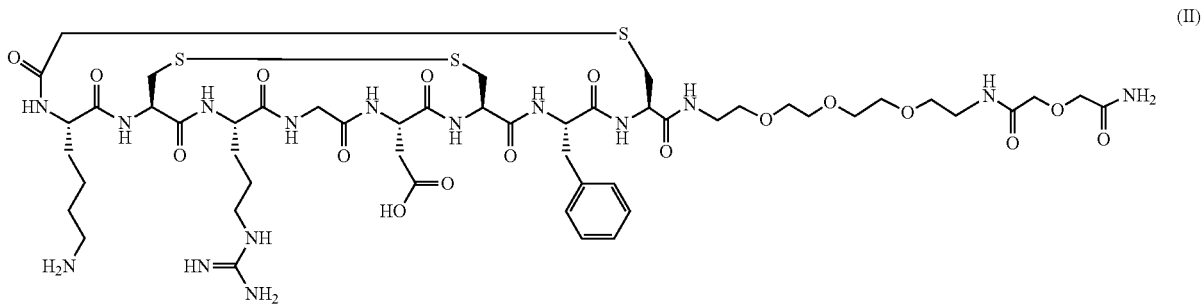 [SMILES: N=C(N)NCCC[C@@H]1NC(=O)[C@@H]2CSSC[C@H](NC(=O)[C@H](CC(=O)O)NC(=O)CNC1=O)C(=O)N[C@@H](Cc1ccccc1)C(=O)N[C@H](C(=O)NCCOCCOCCOCCNC(=O)COCC(N)=O)CSCC(=O)N[C@@H](CCCCN)C(=O)N2]
(II)
to form compound (IIIa):
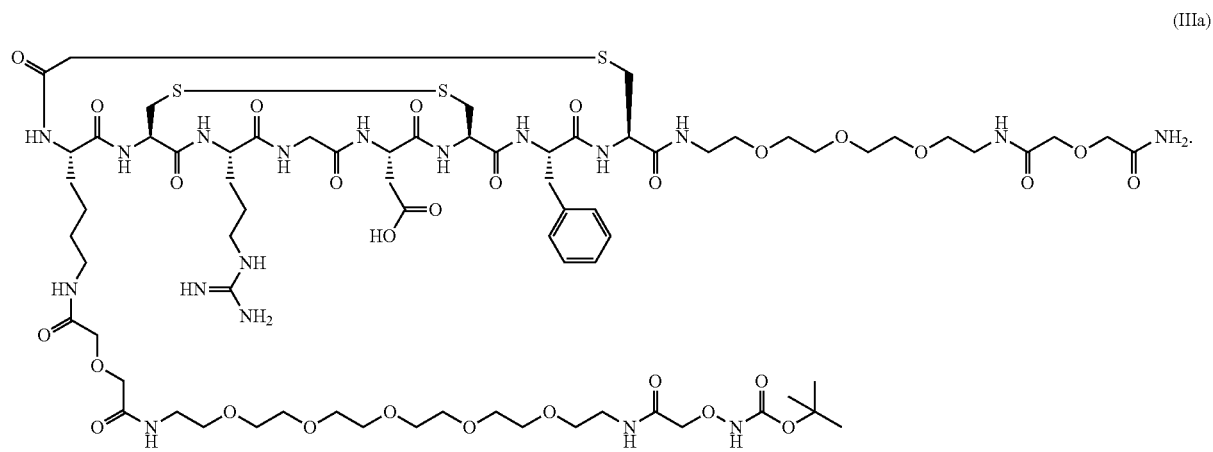 [SMILES: CC(C)(C)OC(=O)NOCC(=O)NCCOCCOCCOCCOCCOCCNC(=O)COCC(=O)NCCCC[C@@H]1NC(=O)CSC[C@@H](C(=O)NCCOCCOCCOCCNC(=O)COCC(N)=O)NC(=O)[C@H](Cc2ccccc2)NC(=O)[C@@H]2CSSC[C@H](NC1=O)C(=O)N[C@@H](CCCNC(=N)N)C(=O)NCC(=O)N[C@@H](CC(=O)O)C(=O)N2]
(IIIa)
6. A method for preparing compound (IV), comprising preparing compound (IIIa) according to the method of claim 5, and reacting compound (IIIa):
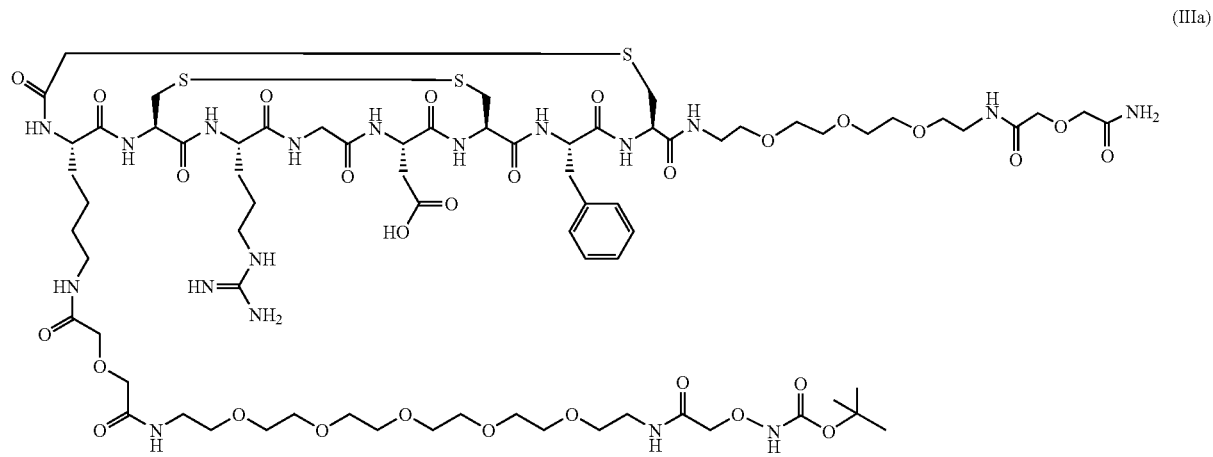 [SMILES: CC(C)(C)OC(=O)NOCC(=O)NCCOCCOCCOCCOCCOCCNC(=O)COCC(=O)NCCCC[C@@H]1NC(=O)CSC[C@@H](C(=O)NCCOCCOCCOCCNC(=O)COCC(N)=O)NC(=O)[C@H](Cc2ccccc2)NC(=O)[C@@H]2CSSC[C@H](NC1=O)C(=O)N[C@@H](CCCNC(=N)N)C(=O)NCC(=O)N[C@@H](CC(=O)O)C(=O)N2]
(IIIa)

with 4-$^{18}$F fluorobenzaldehyde to form compound (IV)

(IV)

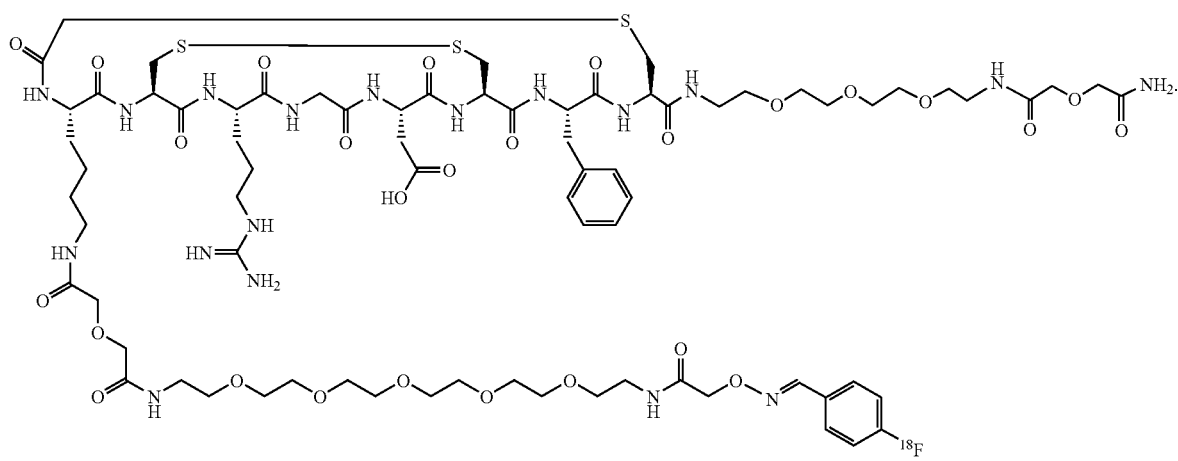

7. The method according to claim 1, wherein R is $CH_3$—$C_6H_4$— and n is 3 and p-toluene sulfonylchloride reacted with 1,11-dihydroxy-3,6,8-trioxa-undecane, (B), at a temperature in the range 15° C. to 27° C. for 6 to 15 hours to form 11-O-tosyl-3,6,9-trioxa-1-hydroxy-undecane, (C).

8. The method according to claim 7, wherein the temperature is 22° C. and the reaction time is 8 hours.

9. The method according to claim 7, wherein 11-O-tosyl-3,6,9-trioxa-1-hydroxy-undecane, (C), was dissolved in dimethyl-formamide and potassium phthalimide stirred into the solution for 6 to 15 hours at a temperature range of 70° C. to 100° C. to form N-(3,6,9-trioxa-11-hydroxy-undecane)-phthalimide, (D).

10. The method according to claim 9, wherein 80 to 120 milligrams of compound (D) was dissolved in methanol and hydrazine monohydrate was added and then heated to 30° C. to 80° C. for 1 to 5 hours and then cooled to room temperature and stirred for about 6 to 15 hours, forming 11-amino-3,6,9-trioxa-hydroxy-undecane, (E).

11. The method according to claim 10, wherein (E) was mixed with 1.0 mole of dichloromethane, 1.0 mole of dimethyl-formamide, and 1.5 moles of diglycolic anhydride and heated to a temperature range of 30° C. to 50° C. for 1 to 3 hours, then adjusted to a pH of 9 to 15 with 1 mole of NaOH(aq) thus forming 17-hydroxy-3,9,12,15-tetraoxa-6-aza-5-oxo-heptadecanoic acid, (F).

12. The method according to claim 1, wherein (PG-aminoxy)acetic acid, (G), is dissolved in acetic anhydride and heated to a temperature in the range 40° C. to 70° C. for 48 to 72 hours to form (PG-aminooxy) acetic anhydride, (H).

13. The method according to claim 12, wherein formula (H) was dissolved in tetrahydrofuran, 2-(2-aminoethoxy) ethanol added and stirred at room temperature for about 2 to 4 days, then mixed with water and the pH adjusted to 9 to 12 with NaOH (aq) and stirred for 6 to 15 hours to form 5-N-(PG-aminooxy-acetamide)-3-oxa-1-hydroxypentane, (I).

14. The method according to claim 1, wherein the base used in the reaction of formulae (F) and (J) is lithium diisopropylamine.

15. The method according to claim 1, wherein R1=9-fluorenylmethyl wherein PG is 9-fluorenylmethoxycarbonyl.

16. The method according to claim 1, wherein R1=tert-butyl where PG is Boc, t-butoxycarbonyl (—COOCH($CH_3$)).

17. The method according to claim 1, wherein either R2=H where PG is formyl or R2 is methyl wherein PG is acetyl.

18. The method according to claim 1, wherein R2=phenyl where PG is benzoyl.

19. The method according to claim 1, wherein PG is allyl.

20. The method according to claim 1, wherein PG is benzyl.

* * * * *